(12) United States Patent
Reel

(10) Patent No.: US 6,921,908 B2
(45) Date of Patent: Jul. 26, 2005

(54) METHODS FOR FLUORESCENCE DETECTION THAT MINIMIZES UNDESIRABLE BACKGROUND FLUORESCENCE

(75) Inventor: Richard T. Reel, Hayward, CA (US)

(73) Assignee: Applera Corporation, Foster City, CA (US)

( * ) Notice: Subject to any disclaimer, the term of this patent is extended or adjusted under 35 U.S.C. 154(b) by 0 days.

(21) Appl. No.: 10/833,425

(22) Filed: Apr. 28, 2004

(65) Prior Publication Data

US 2004/0200979 A1 Oct. 14, 2004

Related U.S. Application Data

(63) Continuation of application No. 10/055,517, filed on Jan. 23, 2002, now abandoned.

(51) Int. Cl.[7] .............................................. F21V 9/16
(52) U.S. Cl. .............................. 250/458.1; 250/459.1; 250/461.1
(58) Field of Search .......................... 250/458.1, 459.1, 250/461.1

(56) References Cited

U.S. PATENT DOCUMENTS

| | | | |
|---|---|---|---|
| 4,811,218 A | | 3/1989 | Hunkapiller et al. |
| 5,062,942 A | * | 11/1991 | Kambara et al. ............ 356/344 |
| 5,323,008 A | | 6/1994 | Studholme et al. |
| 5,324,401 A | * | 6/1994 | Yeung et al. ................ 356/344 |
| 5,355,215 A | | 10/1994 | Schroeder et al. |
| 5,424,841 A | * | 6/1995 | Van Gelder et al. ...... 250/458.1 |
| 5,452,090 A | | 9/1995 | Progler et al. |
| 5,498,324 A | * | 3/1996 | Yeung et al. ................ 356/344 |
| 5,543,026 A | * | 8/1996 | Hoff et al. .................... 204/612 |
| 5,591,981 A | * | 1/1997 | Heffelfinger et al. ..... 250/458.1 |
| 5,784,152 A | * | 7/1998 | Heffelfinger et al. ..... 250/458.1 |
| 5,818,582 A | * | 10/1998 | Fernandez et al. ........ 250/458.1 |
| 5,834,758 A | * | 11/1998 | Trulson et al. ............ 250/458.1 |
| 5,972,716 A | | 10/1999 | Ragusa et al. |
| 6,211,954 B1 | * | 4/2001 | Danielzik et al. ......... 250/458.1 |
| 6,222,664 B1 | | 4/2001 | Dorsel |
| 6,252,236 B1 | * | 6/2001 | Trulson et al. ............ 250/458.1 |
| 6,300,638 B1 | * | 10/2001 | Groger et al. ............ 250/458.1 |

OTHER PUBLICATIONS

Joseph R. Lakowicz, "Principles of Fluorescence Spectroscopy," *First Printing Sep.*, 1983, Chapter 3, pp. 53–56, 81–85, Plenum Press—New York and London.

John W. Simpson, et al., "A Transmission Imaging Spectrograph and Microfabricated Channel System for DNA Analysis," *Electrophoresis* 2000, 21, 135–149.

Richard T. Reel, "Camera Lens Spectrograph Optics Design for MegaGUT," Jan. 16, 1997, pp. 1–33.

* cited by examiner

*Primary Examiner*—Christopher W. Fulton
*Assistant Examiner*—Travis Reis

(57) ABSTRACT

The present invention provides a method for the excitation of a fluorescent sample and the measurement of the fluorescent emission. The method of the present invention has the advantage of significantly reducing the amount of background fluorescence. The method includes the steps of exciting a sample in a substrate with a beam of light that enters the substrate at an angle less than or equal to 45° C., and preferably, less than or equal to 20°, and then collecting the fluorescent emission form the sample with a lens system which focuses the emitted light onto a CCD for detection. Although the following description of the present invention uses a scanning system using channel plates by way of illustration, the method described herein may also be used with non-scanning systems as well as capillary systems.

24 Claims, 2 Drawing Sheets

METHODS FOR FLUORESCENCE DETECTION THAT MINIMIZES UNDESIRABLE BACKGROUND FLUORESCENCE

CROSS-REFERENCE TO RELATED APPLICATIONS

This application is a continuation of U.S. patent application Ser. No. 10/055,517, filed Jan. 23, 2002 now abandoned, which is incorporated by reference.

FIELD OF THE INVENTION

This invention relates generally to fluorescence analytical techniques. More specifically, the invention relates to a method and apparatus for detecting a fluorescent sample that minimizes undesirable background.

BACKGROUND OF THE INVENTION

Fluorescence detection is widely used in biochemical and medical research applications due to its high sensitivity. For example, fluorescence detection is used in automated DNA sequencing, capillary electrophoresis and a variety of immunoassays. In response to excitation, fluorescent biomolecules and dyes emit light at characteristic wavelengths, which differ from the excitation wavelength. By detecting these characteristic wavelengths, the composition of a sample can be determined.

In many biological applications, the amount of sample to be detected is usually quite small. Over the years, methods and apparatus have been able to manipulate and separate on smaller and smaller scales, going from the $\mu$M range to nM and pM ranges. As the sample size decreases, the background fluorescence becomes more significant in relation to the fluorescence of the sample.

The dominant background noise source in fluorescence detectors is often shot noise. Shot noise comes from the sample and background fluorescence. The background fluorescence comes from fluorescence or Raman scattering from the sample as well as from the substrate that the sample is contained in. High background fluorescence also reduces the dynamic range of the detector by causing saturation of the detector. Therefore, reducing the background noise is one strategy for improving the performance of fluorescence detectors.

SUMMARY OF THE INVENTION

The present invention provides a method for the excitation of a fluorescent sample and the measurement of the fluorescent emission that significantly reduces the amount of background fluorescence. The method includes the steps of exciting a sample in a substrate with a beam of light that enters the substrate at an angle less than or equal to about 45°, and more preferably, less than or equal to about 20° and collecting the fluorescent emission from the sample with a lens system which focuses the emitted light onto a charge coupled device (CCD) for detection.

The beam of light is generated from a laser and is directed to the sample-containing substrate by a scanning mirror and a prism. The light enters the substrate at an angle less than or equal to about 45°, and more preferably, less than or equal to about 20° with respect to the axis of the channel plates and continues through the channel plate into the sample. In another embodiment, a lens system collects and collimates the fluorescence emitted by the excited sample. The collected light then passes through a wide bandpass filter to exclude scattered laser light. The collected light then passes through a transmission grating which disperses the light in the spectral axis, which is oriented perpendicular to the axis of the substrate. The image is then focused onto a scientific grade CCD for detection.

The method of the present invention can be used with a scanning system or a non-scanning system. Non-limiting examples of application of the present invention are scanning systems using channel plates and capillary systems such as capillary electrophoresis.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The various advantages of the present invention will become apparent to one skilled in the art by reading the following specification and subjoined claims and by referencing the following drawings in which:

DETAILED DESCRIPTION OF THE PREFERRED EMBODIMENTS

The present invention provides a method for the excitation of a fluorescent sample and the measurement of the fluorescent emission. The method includes the steps of exciting a sample in a substrate with a beam of light that enters the substrate at an angle less than or equal to about 45° C., and more preferably, less than or equal to about 20°, and then collecting the fluorescent emission from the sample with a lens system which focuses the emitted light onto a CCD for detection. Although the following description of the present invention uses a scanning system using channel plates by way of illustration, the method described herein may also be used with non-scanning systems as well as capillary systems.

In one embodiment of the invention, the beam of light is directed to the channel by a scanning mirror and prism. The excitation beam can be generated by a UV, visible or infrared light source, preferably by a laser. The angle of the mirror can be adjusted to control the angle that the excitation beam enters the channel. Preferably, the excitation beam enters the channel at an angle less than or equal to about 45°, and more preferably, less than or equal to about 20°. The optimal angle for the incident beam will depend on the index of refraction of the material of the channel plate. Generally, the more shallow the angle, the greater the amount of sample fluorescence collected along with a concomitant reduction in the background fluorescence.

In another embodiment of the present invention, a first lens system collects and collimates the fluorescence from the excited sample into parallel rays. Preferably the lens is situated perpendicular to the channel axis. The collecting lens may be a simple camera lens. The collected light then passes through a long pass or wide bandpass filter, which removes scattered light at the laser wavelength. The remaining filtered light, which consists essentially of fluorescence from the sample and background from the channel, then passes through a transmission defraction grating. The transmission grating separates the light into rays of differing wavelength that diverges along the direction of the spectral axis, perpendicular to the channel axis. Finally a focusing lens directs the light onto the CCD.

Figure 1:
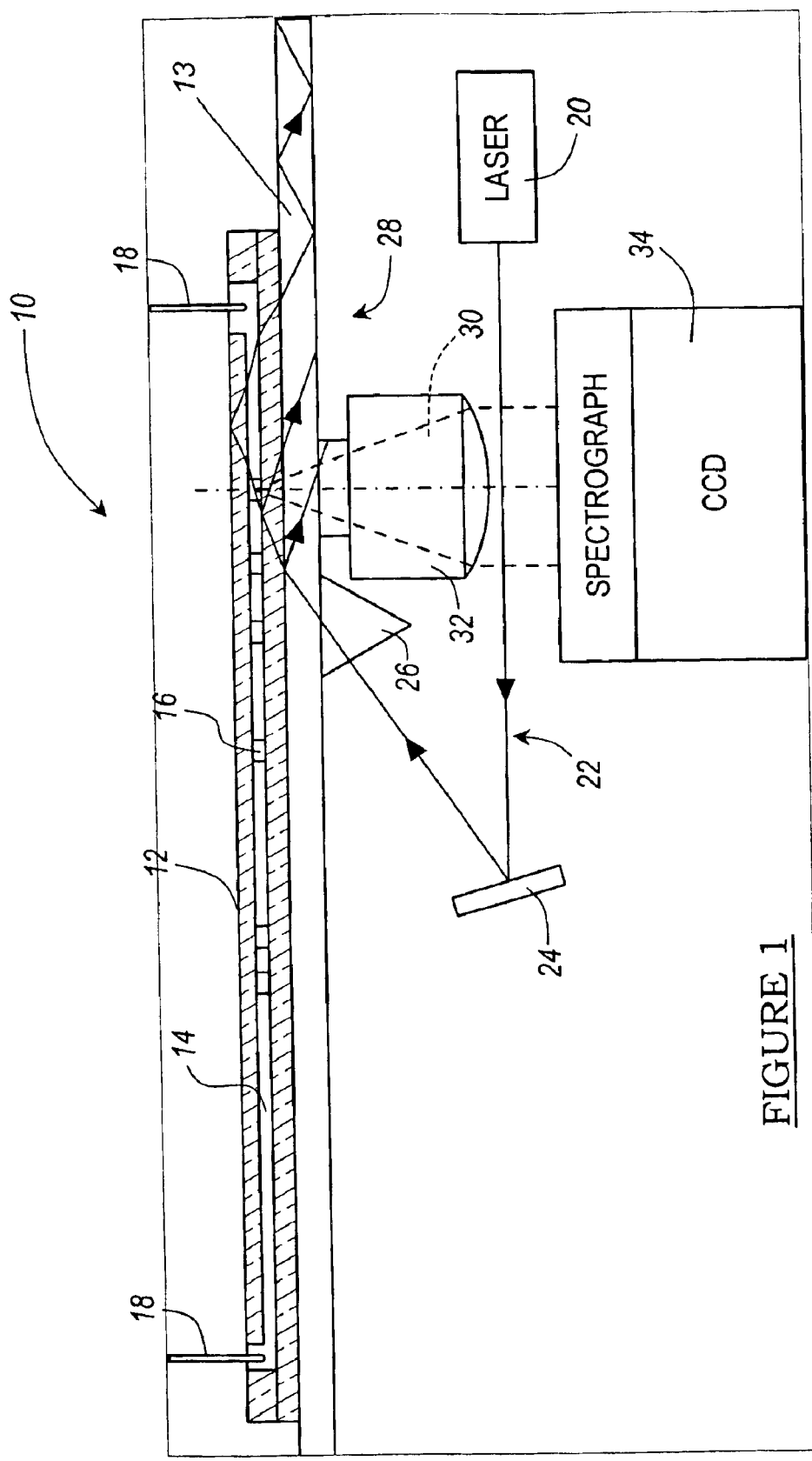
FIG. 1 is a schematic block diagram illustrating a fluorescence detection system.
Figure 2:
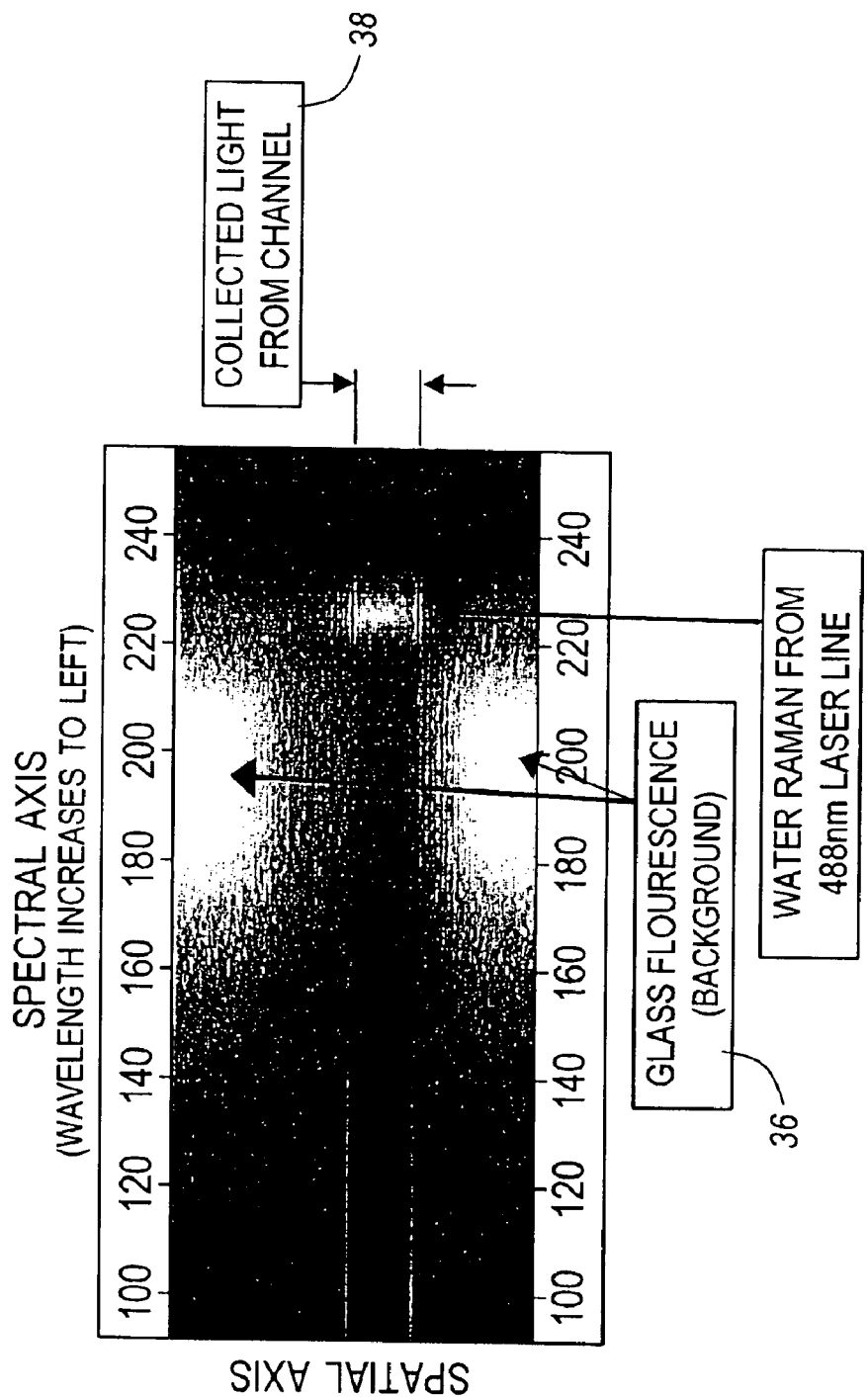
FIG. 2 is a photograph showing the CCD image generated following exposure to an excitation beam of light.

In a further embodiment, the image from the CCD is collected to bin or read out as a data file. Preferably, only the section of the image on the CCD associated with the fluorescence of the sample is collected by selection of the appropriate pixels to bin and read out. In the method of the present invention, as the excitation beam moves through the plate at an angle, the excitation beam creates a fluorescent trail. When this trail is imaged by the collection optics, the fluorescence from different parts of the channel will fall on different sections of the spatial axis of the CCD. As illustrated in FIG. 2, the fluorescence associated with the sample is separated from the background fluorescence An apparatus for performing the above-described methods of the present invention is shown in FIG. 1. FIG. 1 illustrates an apparatus 10 for use with a scanning system using a channel plate 12. The channel plate 12 defines a channel 14 which receives a medium that contains samples 16. A current is applied to the medium that contains the samples 16 by means of a pair of electrodes 18. Upon passing a current through the medium, the samples 16 are separated as is known in the electrofluorescence art. The channel plate 12 may be formed from glass, fused silica, plastic or other transparent type material. The channel plate 12 is supported by a support plate 13 formed from glass, fused silica, plastic or other transparent material. In addition, the channel 14 may be defined by other suitable structures such as capillary tubes, arrays of capillary tubes and slab gel with field defined lanes.

A laser 20 generates an excitation beam 22 that is essentially parallel to the channel plate 12 and directed toward a reflective mirror 24. The mirror 24 is adjusted to reflect the excitation beam 22 at the desired angle into the channel plate 12. Here again, the excitation beam 22 enters the channel plate 12 at an angle less than or equal to about forty-five degrees (45°), and preferably less than or equal to about twenty degrees (20°). The excitation beam 22 is directed through a prism 26 to facilitate entry of the excitation beam 22 into the support plate 13. The support plate 13 is optically coupled to the channel plate 12 using water, direct contact or any transparent material with an index similar to the channel plate. The focused excitation beam 22 enters the channel plate 12 and passes through the channel plate 12 before reaching the channel 14 containing the sample 16. The focused excitation beam 22 continues through the top layer of the channel plate 12. As defined by the Fresnel Equations, some light is reflected at boundaries where the index of refraction changes. This creates the reflected beams 28. Both the focused excitation beam 22 and the reflected beam 28 can generate undesirable fluorescent emissions from the samples 16.

A portion of the sample fluorescence emissions 30 enters collection optics 32 where the emitted light is collected, collimated and dispersed before being focused onto CCD 34 using known optics and CCD technology. In this regard, the collection optics 32 includes a first collimating lens, which collects and collimates the fluorescence from the excited sample 16 into parallel rays. The collected light is then passed through a long pass or laser rejection filter, which removes scattered or stray light at the laser wavelength(s). The remaining filtered light, which consists of the fluorescence emissions from the sample 16 and fluorescent background from the channel plate 12 is then passed through a transmission defraction grading, a prism, a prism or reflected off a reflective grating. The transmission defraction grading separates the lights into rays of differing wavelengths that diverges along the direction of the spectral axis which is perpendicular to the axis of the channel 14. Finally, a second focusing lens focuses the light onto the CCD 34. The collection optics 32 may be similar to the optics system disclosed in, U.S. Ser. No. 09/564,790 filed May 5, 2000 or Simpson et al., "A Transmission Imaging Spectrograph and Micro fabricated Channel System for DNA Analysis", *Electrophoresis* 2000, 21, 135–149, both of which are hereby incorporated by reference. However, other suitable optics systems may be used. Further, it will be appreciated other types of defectors can also be used to receive light from the sample 16. These include CMOS detectors, photodiodes, photodiodes arrays, photomultiplier tubes, photomultiplier tube arrays or other suitable detectors. In addition, the preferred orientations of the collection optics 32 is substantially perpendicular to the excitation beam 22 entering the sample 16 as this allows a larger amount of light from the sample to be collected while still rejecting background.

The image from the CCD 34 is collected to be read out as a data file as is shown and illustrated in FIG. 2. In this regard, FIG. 2 illustrates both the glass fluorescence 36, which is the background fluorescence from the channel plate 12, as well as the collected light 38 from within the channel 14 which consists of the fluorescence from the sample 16. This collected light 38 is preferably from the only section of the image on the CCD 34 associated with the fluorescence of sample 16, which is collected by selection of the appropriate detector elements or pixels (which receive little background fluorescence) from which meaningful data is to be read. The CCD 34 may also use "binning" in which the photogenerated charge in adjacent detector elements are read out as a combined charge pocket during a single read. The use of binning may reduce overall noise when compared to other processing techniques, but may be accompanied by loss of spacial resolution.

By allowing the excitation beam 22 to enter the channel plate 12 at an angle of less than about forty-five (45°), and preferably less than or equal to about twenty degrees (20°), much of the reflected light and background fluorescence that is produced by the excitation beam 22 entering the channel plate 12 is directed away from the collection optics as is shown in FIG. 2. Accordingly, because less background noise enters the collection optics 32; the sensitivity of the apparatus 10 is increased. In addition, because the excitation beam 22 enters the plate at a relatively small angle with respect to the collection plate 12, a greater amount of fluorescent light is created by the samples 16 causing an increase in the fluorescence of the sample and therefore improved sensitivity.

The method for selecting which pixels or detector elements are used to generate meaningful data from which spectral information is to be determined, and which pixels or detector elements should be ignored as receiving excessive background fluorescence, involves two considerations. The signal-to-noise ratio of the CCD 34 should be maximized while the dynamic range of the CCD 34 is not excessively limited. One method for selecting which detector elements should be used to generate meaningful data for analysis is as follows.

First, the output from a first group of detector elements near the center of the image on the CCD 34 is recorded and the signal-to-noise ratio determined. Once the signal-to-noise ratio has been determined from this first set of detector elements, the signal-to-noise ratio is compared to the signalto-noise ratio from a second group of detector elements. This second group of detector elements includes those detector elements in the first group as well as detector elements that are adjacent to the detector elements in the first group. If the signal-to-noise ratio increases, this indicates that better data can be obtained if the second group of detector elements is used to generate spectral information as compared to using the first group of detector elements. The output of the second group of detector elements is therefore initially selected to be used to generate meaningful data from which spectral information is to be determined.

This process is continued with progressively larger sets of detector elements until the signal-to-noise ratio begins to decline. When the signal-to-noise ratio begins to decline, the inclusion of additional detector elements does not improve collection of meaningful data and therefore the output from the remaining detector elements is not considered. However, during this process, care must be taken that the background noise does not consume so much of the capacity of the CCD 34 so as to diminish the dynamic range of the CCD 34. If too much of the dynamic range is consumed a lower number of bins should be used.

The foregoing description discloses and describes merely exemplary embodiments of the present invention. For example, the excitation beam 22 could enter the channel plate 12 at an angle greater than 45° if the collection optics 32 is located off-axis (i.e., off-set from the direction perpendicular to the direction of the excitation beam 22 entering the sample). Further, the inside top surface of the channel plate 12 may be coated with a low index material or fabricated from a low index material (e.g., Teflon AF). In such a case, the excitation beam 22 could be orientated at an angle (i.e., about 22°) that would be totally internally reflected so as to further separate the detection region from the background region. Further, multiple excitation beams 22 may be used as well as multiple detection elements. One skilled in the art will readily recognize from such discussion, and from the accompanying drawings that various changes, modifications and variations can be made therein without departing from the spirit and scope of the invention.

What is claimed is:

1. A method for detecting fluorescence from a sample in a channel plate comprising:
    providing an excitation beam of light to the sample and the channel plate, wherein the excitation beam of light produces a fluorescent trail, wherein the fluorescent trail comprises a first portion from the channel plate and a second portion from the sample;
    positioning the excitation beam of light at an angle less than or equal to about 45 degrees relative to a longitudinal axis of the channel plate to increase the spatial resolution between the first portion and the second portion; and
    collecting the second portion on a detector.

2. The method as defined in claim 1, wherein the detector is selected from the group consisting of charge coupled devices, CMOS detectors, photodiode, photodiode array, photomultiplier tubes, and photomultiplier tube arrays.

3. The method as defined in claim 1, wherein the excitation beam of light is positioned at an angle less than or equal to about 20° relative to a channel axis.

4. The method as defined in claim 1, wherein a collection optics system collimates the fluorescent trail and refocuses the second portion onto the detector.

5. The method as defined in claim 4, wherein the collection optics further removes scattered light from the excitation beam using a long pass filter.

6. The method as defined in claim 4, wherein the collection optics further removes scattered light from the excitation beam using a band pass filter.

7. The method as defined in claim 1, wherein positioning comprises directing the excitation beam of light substantially parallel to the channel plate into a reflective mirror, which reflects the excitation beam of light into the sample.

8. The method as defined in claim 7, wherein reflecting further comprises directing the excitation beam of light from the reflective mirror through a prism.

9. An apparatus for detecting fluorescence from a sample in a channel plate comprising:
    a light source operable to generate an excitation beam of light, wherein the excitation beam of light produces a fluorescent trail, wherein the fluorescent trail comprises a first portion from the channel plate and a second portion from the sample;
    a mirror operable to position said excitation beam of light into the sample, increasing the spatial resolution between the first portion and the second portion; and
    a detector operable to image the second portion,
    wherein the mirror, the light source, and the detector are located on the same side of the channel plate.

10. The apparatus as defined in claim 9, wherein the detector is selected from the group consisting of charge coupled devices, CMOS detectors, photodiode, photodiode array, photomultiplier tubes, and photomultiplier tube arrays.

11. The apparatus as defined in claim 9, further comprising collection optics, wherein the collection optics comprises a long pass filter operable to remove scattered light at a wavelength of said excitation beam of light.

12. The apparatus as defined in claim 9, further comprising collection optics, wherein the collection optics comprises a transmission defraction grating operable to separate light into differing wavelengths.

13. The apparatus as defined in claim 9, further comprising a prism operable to direct the excitation beam of light toward the sample.

14. The apparatus as defined in claim 9, wherein the light source is a laser.

15. A method for detecting fluorescence from a sample in a channel plate comprising:
    providing an excitation beam of light to the sample and the channel plate, wherein the excitation beam of light produces a fluorescent trail, wherein the fluorescent trail comprises a first portion from the channel plate and a second portion from the sample;
    positioning the excitation beam of light at an angle less than or equal to about 45 degrees relative to a longitudinal axis of the channel plate to increase the spatial resolution between the first portion and the second portion; and
    collecting the second portion and substantially smaller amounts of the first portion on a detector.

16. The method as defined in claim 15, wherein the excitation beam is positioned at an angle less than or equal to about 20° relative to a channel axis.

17. The method as defined in claim 15, wherein providing an excitation beam of light comprises providing a laser to generate the excitation beam of light.

18. The method as defined in claim 15, wherein positioning comprises directing the excitation beam of light substantially parallel to the channel plate into a reflective mirror, which reflects the excitation beam of light into the sample.

19. The method as defined in claim 18, wherein reflecting further comprises directing the excitation beam of light from the reflective mirror through a prism.

20. A method for detecting fluoresence from a sample in a channel plate comprising:
- providing an excitation beam of light to the sample and the channel plate, wherein the excitation beam of light produces a fluorescent trail, wherein the fluorescent trail comprises a first portion from the channel plate and a second portion from the sample;
- positioning the excitation beam of light at angle less than or equal to about 45 degrees relative to a longitudinal axis of the channel plate to increase the spatial resolution between the first portion and the second portion; and
- collecting the first portion and the second portion on spatially different sections of a detector.

21. The method as defined in claim 20, wherein the excitation beam is positioned at an angle less than or equal to about 20° relative to a channel axis.

22. The method as defined in claim 20, further comprising:
- providing a light source operable to generate the excitation beam of light; and
- providing a mirror operable to position the excitation beam of light.

23. An apparatus for detecting fluorescence from a sample in a channel plate comprising:
- a light source operable to generate an excitation beam of light, wherein the excitation beam of light produces a fluorescent trail, wherein the fluorescent trail comprises a first portion from the channel plate and a second portion from the sample;
- a mirror operable to position said excitation beam of light into the sample, increasing the spatial resolution between the first portion and the second portion;
- collection optics to collimate and focus the fluorescent trail; and
- a detector operable to image the second portion,
- wherein the mirror, the light source, and the detector are located on the same side of the channel plate.

24. The apparatus according to claim 23, wherein the collection optics are oriented about 90 degrees with respect to a channel axis.

* * * * *